United States Patent
Livet et al.

[11] Patent Number: 6,099,570
[45] Date of Patent: Aug. 8, 2000

[54] KNEE JOINT PROTHESIS

[75] Inventors: Pacsal Livet; Heribert Frei, both of Winterthur; René Brack, Cham, all of Switzerland

[73] Assignee: Sulzer Orthopaedie AG, Baar, Switzerland

[21] Appl. No.: 09/179,253

[22] Filed: Oct. 26, 1998

[30] Foreign Application Priority Data

Oct. 28, 1997 [EP] European Pat. Off. .............. 97810802

[51] Int. Cl.[7] .................................. A61F 2/38
[52] U.S. Cl. .................... 623/20.21; 623/20.27
[58] Field of Search ............... 623/20, 20.21, 623/20.27

[56] References Cited

U.S. PATENT DOCUMENTS

| | | | |
|---|---|---|---|
| 4,136,405 | 1/1979 | Pastrick | 623/20 |
| 4,301,553 | 11/1981 | Noiles | 623/20 |
| 4,950,297 | 8/1990 | Elloy | 623/20 |
| 5,370,701 | 12/1994 | Finn | 623/20 |
| 5,395,401 | 3/1995 | Bahler . | |
| 5,405,395 | 4/1995 | Coates . | |
| 5,824,096 | 10/1998 | Pappas | 623/20 |
| 5,879,392 | 3/1999 | McMinn | 623/20 |
| 5,954,770 | 9/1999 | Schmotzer | 623/20 |

FOREIGN PATENT DOCUMENTS

| | | |
|---|---|---|
| 0724868A1 | 8/1996 | European Pat. Off. . |
| 4434806A1 | 4/1996 | Germany . |
| 2296443A | 7/1996 | United Kingdom . |

*Primary Examiner*—Michael J. Milano
*Attorney, Agent, or Firm*—Townsend and Townsend and Crew LLP

[57] ABSTRACT

A knee joint prosthesis (1) comprises a tibia part (1) having a tibia bearing surface (10) and a bearing body (3) which is slidingly displaceably journalled on the tibia bearing surface (10) and which has bearing scallops (31) on its side which is remote from the tibia bearing surface (10). Furthermore, it comprises a femur part (5) which is movably arranged on the bearing scallops (31) of the bearing body (3) as well as comprising a guide piece (2) which is arranged to be rotationally fixed relative to the tibia part (1) and which permits only a displacement of the bearing body (3) in the sagittal direction relative to the tibia bearing surface (1). Furthermore, it comprises a coupling member which cooperates both with the guide piece (2) and with the femur part (5) and permits a rotation of the femur part (5) on the bearing body (3). The coupling member has a rotatably journalled pin (4) which extends in the direction of the longitudinal axis (14) of the tibia part (1) or of an axis of rotation parallel to it or in the direction of an axis which is inclined relative to the longitudinal axis of the tibia part (1) or to an axis of rotation parallel to it.

12 Claims, 7 Drawing Sheets

KNEE JOINT PROTHESIS

BACKGROUND OF THE INVENTION

The invention relates to a knee joint prosthesis in accordance with the preamble of the independent claim.

Knee joint prostheses are available today in a large variety of various designs, with their principles of functioning often differing greatly from one another. This is related—among other things—to whether and, where appropriate, which ligaments (e.g. cross ligaments, lateral ligaments) are present and still capable of functioning in the respective patient in whom the prosthesis is to be implanted.

A knee joint prosthesis of this kind is disclosed for example in EP-A-0,724,868. The knee joint prosthesis described there comprises a tibia part which is anchored in the tibia and which has a tibia bearing surface on which a bearing body in the form of a meniscus part is slidingly displaceably arranged. The path along which the meniscus part is guided is limited in several exemplary embodiments (e.g. FIGS. 1a, 1b, 1c) to the anterior/posterior direction. For this purpose the tibia part is provided with a guide part or guide piece which engages in a corresponding guide part (elongate hole or dove-tail groove) in the meniscus part, through which the meniscus part is displaceable only in the anterior/posterior direction.

The guide piece which is provided at the tibia part has a bar-shaped prolongation which points in the proximal direction, thus in the direction of the femur part. This bar-shaped prolongation extends in a direction parallel to the longitudinal axis of the tibia part. A coupling member in the form of a cylindrical bolt which has a passage bore extending perpendicular to the longitudinal axis of the bolt is provided for the coupling of this prolongation and thus of the guide pieces provided on the tibia part to the femur part.

The femur part has two condyles which can move on the corresponding bearing scallops (bearing surfaces) of the bearing body. The femur part further has two side walls, in each of which a cylindrical cut-out is provided which breaks through the side wall.

The above described cylindrical bolt with its passage bore extending perpendicular to the longitudinal axis of the bolt is inserted into these cut-outs in the side walls and the bar shaped prolongation of the guide piece is passed through the cylindrical bore of the bolt. The bolt thus acts as a coupling member because it couples the femur part to the prolongation on the guide piece during the flexion and extension movement of the knee. During the extension and/or flexion of the knee the cylindrical bolt slides upwards (extension) or downwards (flexion) respectively along the prolongation on the guide piece. At the same time the meniscus part is displaced in the anterior (extension) or posterior direction (flexion) respectively.

The knee joint prosthesis described in EP-A-0,724,868 is absolutely capable of functioning from the point of view of its principle. The assembly of the prosthesis in the operating room is not completely simple for the surgeon, however, because the bar-shaped prolongation of the guide piece must be guided through the bore in the cylindrical bolt after the tibia part has been fixed in the tibia and the femur part has been fixed in the femur, thus practically a kind of "threading procedure" must be carried out. This can cause difficulties for the surgeon under certain circumstances since the tibia part and the femur part are of course already fixed in the corresponding bones.

Moreover, the following case, which is described with reference to FIG. 1, can however also arise in the prosthesis described in EP-A-0,724,868. During flexion the cylindrical bolt B moves downwards along the bar shaped prolongation S of the guide piece F while the meniscus part M moves in the posterior direction. The case can now arise that the femur lies in contact with the rear end E of the meniscus part M although a complete bending has not occurred. If one were now to attempt to carry out a further bending, the center of rotation would have to be formed by the rear end E of the meniscus part M. This would mean that the cylindrical bolt B would have to move into the position indicated in broken lines during a further bending. This cannot take place however because the bolt B can of course only be moved upwards and downwards along the prolongation S of the guide piece F (and not on a circular path as it would have to be). The result is a blocking of the prosthesis, which prevents a further flexion. In worse cases, when the forces are sufficiently large, the result can even be a loosening of the femur part of the prosthesis.

SUMMARY OF THE INVENTION

It is thus the object of an invention to propose a knee joint prosthesis of the named kind in which the above described problems are avoided, in which thus in particular a flexion is possible without problem. Moreover, the prosthesis should be easy to assemble during the operation, thus in particular when the tibia part and the femur part have already been fixed to the associated bones. The prosthesis should be reliable to a high degree and it should above all also be suitable for patients in whom both the cross ligaments and the lateral ligaments are either no longer present or are no longer capable of functioning.

This object is satisfied by the knee joint prosthesis in accordance with the invention. The knee joint prosthesis in accordance with the invention comprises a tibia part having a tibia bearing surface. It further comprises a bearing body (meniscus part) which is slidingly displaceably journalled on the tibia bearing surface and which has bearing scallops on its side remote from the tibia bearing surface. Furthermore, it comprises a femur part which is movably arranged on the bearing scallops of the bearing body as well as a guide piece which is arranged to be rotationally fixed relative to the tibia part and which permits only a displacement of the bearing body in the sagittal direction relative to the tibia bearing surface. Finally, the knee joint prosthesis in accordance with the invention also comprises a coupling member which cooperates both with the guide piece and with the femur part and which permits a rotation of the femur part on the bearing body. This coupling member has a rotatably journalled pin which extends in the direction of the longitudinal axis of the tibia part or of an axis of rotation parallel to it or in the direction of an axis which is inclined relative to the longitudinal axis of the tibia part or to an axis of rotation parallel to it. The initially described problems in the flexion are avoided with a prosthesis of this kind because the center of rotation is not restricted to a fixed upwards and/or downwards direction. Moreover, a knee joint prosthesis of this kind is simple to assemble during the operation, and it is in particular also suitable for patients in whom both the cross ligaments and the lateral ligaments are either no longer present or are no longer capable of functioning.

In one exemplary embodiment of the knee joint prosthesis in accordance with the invention the pin which serves as a coupling member has a stabilization piece at its end near the femur part and the femur part has corresponding stabilization surfaces which cooperate with the stabilization piece. A varus/valgus stabilization is achieved in this manner so that a lateral tilting of the femur part and the tibia part relative to one another is prevented.

In a further exemplary embodiment the pin serving as a coupling member is received by a bore provided in the guide piece in which it is rotatably journalled. In this situation, for example, the guide piece can be formed directly on the tibia part.

In a further exemplary embodiment both the guide piece and the coupling member are formed as separate pins, with both the pin serving as a guide piece and the tibia part having means for the rotationally fixed arrangement of the pin serving as a guide piece in the tibia part. The pin serving as a guide piece is thus anchored in a rotationally fixed manner in the tibia part, whereas the pin serving as a coupling member is rotatably journalled. The pins can thus be manufactured separately, through which in particular the manufacture of the guide piece is simple, but also the manufacture of the tibia part, in particular the tibia bearing surface, is simple.

In a further exemplary embodiment the tibia part has an anchoring section which can be connected to a separate anchoring shaft; in a yet further exemplary embodiment the femur part has an anchoring section which can be connected to a separate anchoring shaft. It is thereby possible to use an anchoring section which has a length which is particularly ideal for the respective patient. The definitive decision for the ideal anchoring shaft can even be made during the operation when the surgeon is able to precisely recognize the actual anatomical relationships.

The invention will be explained in the following with reference to the drawings.

DESCRIPTION OF THE PREFERRED EMBODIMENTS

Figure 1:
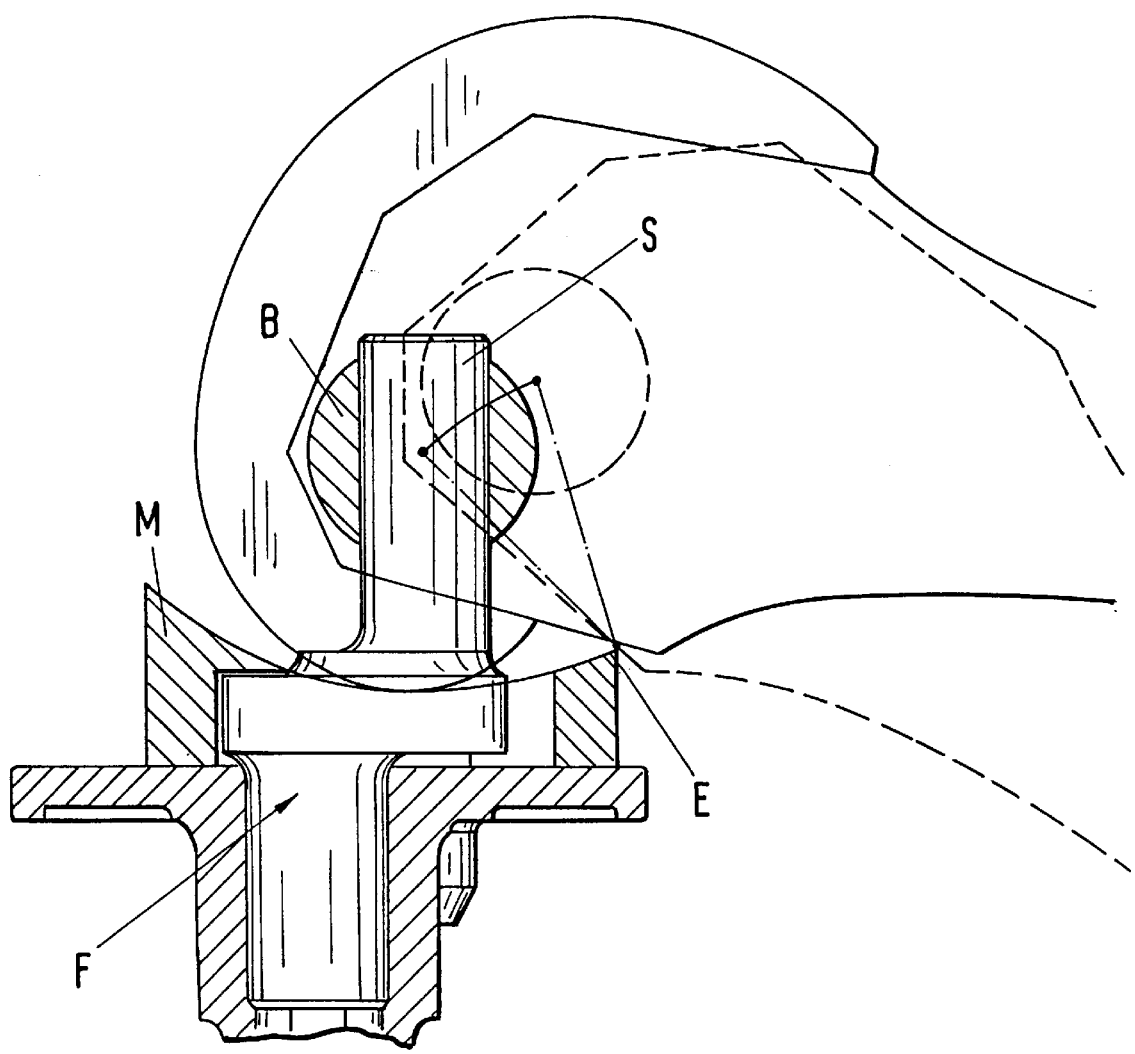
FIG. 1 shows the prosthesis known from EP-A-0,724,868 in different positions.
Figure 2:
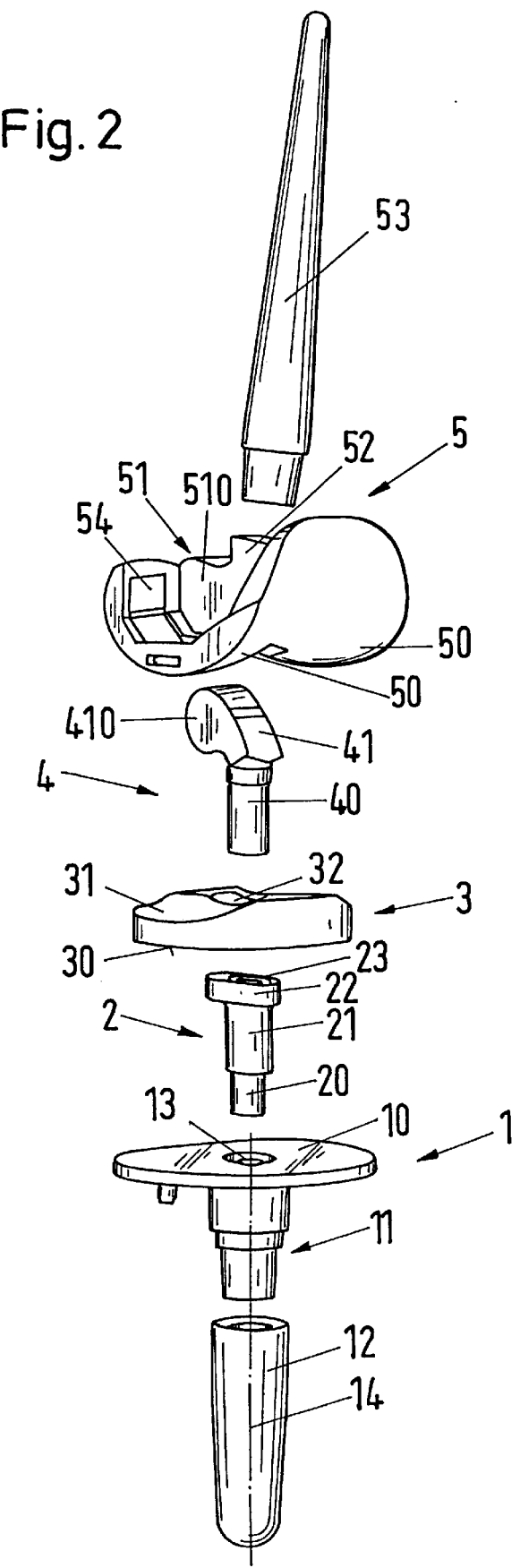
FIG. 2 is an exploded view of an exemplary embodiment of a knee joint prosthesis in accordance with the invention.

In the exploded view of an exemplary embodiment of a knee joint prosthesis in accordance with the invention in FIG. 2 one recognizes the essential parts of the knee joint prosthesis. Essentially, these are a tibia part 1, a pin 2, a bearing body 3, a further pin 4 and a femur part 5.

Considered in somewhat more detail, one recognizes a (usually metallic) tibia part 1 with a tibia bearing surface 10 which is formed in the exemplary embodiment shown as a planar surface which can, however, also be curved in principle. The tibia part 1 further has an anchoring section 11 which can be connected to an anchoring shaft 12, for example by means of a conical connection. In the tibia part 1 a bore 13 which is executed as a blind hole can also be recognized.

The pin 2, which is executed as a guide piece, can be inserted into the bore 13, which is executed as a blind hole, of the tibia part 1. The (typically metallic) pin 2 has three regions here: a lower region 20, a middle region 21 and an upper region 22. In the exemplary embodiment shown in FIG. 2 the outer shape of the lower region 20 is formed as an oval (and will be shown more precisely in reference to FIG. 3 and FIG. 4). In order that the pin 2 can be inserted into the bore 13 of the tibia part 1 the corresponding region of the bore 13 must likewise have an oval shape in the exemplary embodiment described here (which can be produced, for example, by milling). During the insertion of the pin 2, the lower region 20 and the middle region 21 of the pin are received by the bore 13 in the tibia part 1. The pin 2 in the tibia part 1 is arranged to be rotationally fixed by the lower, oval region 20, which is received by the corresponding oval region of the bore 13; it can thus not rotate relative to the tibia part 1 after being inserted. The upper region 22 of the pin 2 lies on the tibia bearing surface 10. The bore 13 in the tibia part 1 is arranged in this situation in such a manner that when the pin 2 is introduced into the bore 13 the upper region 22 of the pin 2 extends in the sagittal direction. Finally, one also recognizes that the pin 2 likewise has a bore 23 which is executed as a blind hole. It is immediately evident that instead of the lower region, the middle region 21 and the corresponding region of the bore in the tibia part 1 can also be made oval so that the rotationally fixed arrangement is produced by the middle region of the pin 2 and the associated part of the bore in the tibia part 1. Cases will even be explained further below in which the rotationally fixed arrangement of the pin 2 in the tibia part 1 is produced with the help of the upper region 22 (and of special means).

The bearing body 3 serving as the meniscus part, usually manufactured of a plastic such as polyethylene, has at its lower side facing the tibia part 1a (here, planar) sliding surface 30 corresponding to the tibia bearing surface 10 so that the bearing body 3 can slide on the tibia bearing surface 10. Furthermore, the bearing body 3 is provided with two bearing scallops 31 which face the femur part and which are integral constituents of the bearing body 3 here (the bearing body is thus in a single piece in the exemplary embodiment described). They can however also be formed as bearing scallops which can be separately manufactured and inserted in a bearing body which is shaped as an eyeglass frame and then, together with the latter, form the meniscus part. The bearing body further has an elongate hole 32, the width of which is dimensioned in such a manner that it can receive the upper region 22 of the pin 2 and, where appropriate, has a smaller clearance. The length of the elongate hole 32 is dimensioned in such a manner that the elongate hole 32 is longer by a predetermined amount than the upper region 22 of the pin 2, with this predetermined amount being dimensioned in such a manner that the bearing body 3 can be displaced in the sagittal direction by a predeterminable amount during the flexion. The pin 2 thus acts as a guide part with respect to the bearing body 3 and allows in particular only a displacement of the bearing body 3 on the tibia bearing surface 10 in the sagittal direction to the rear.

A further pin 4 has a circular cylindrical section 40 and a stabilization piece 41 adjoining it. The stabilization piece 41 in turn is distinguished in particular by two side walls 410, of which only one can be seen in FIG. 2. These side walls 410 of the stabilization piece 41 of the pin 4 cooperate with corresponding stabilization surfaces of the femur part 5 and effect a varus/valgus stabilization of the femur part 5 relative to the tibia part 1.

The femur part 5 has two condyles 50 which cooperate with the bearing scallops 31 of the bearing body 3. These condyles 50 have different radii of curvature and in addition their centers of rotation are also different during the flexion. In the extension the condyles 50 are to a large extent congruent to the bearing scallops 31 and the contact between the condyles 50 and the bearing scallops 31 has a large area; in the flexion, on the other hand, the contact between the condyles 50 and the bearing scallops 31 is distributed over a small area only, or even has the shape of a line, because the radius of curvature in the region of the condyles 50 which is in contact with the bearing scallops 31 during the flexion is significantly less than the radius of curvature of the bearing scallops 31.

The femur part 5 further has a stabilization box 51 which has in particular two stabilization surfaces 510, of which only one can be seen in FIG. 2 as a result of the illustration chosen. These stabilization surfaces 510 cooperate with the side walls 410 of the stabilization piece 41 of the pin 4 and effect the already mentioned varus/valgus stabilization of the femur part 5 relative to the tibia part 1.

Furthermore, the femur part 5 has an anchoring section 52 which can be connected to an anchoring shaft 53, for example by means of a conical connection. Finally, the femur part 5 also has several receptacles 54 on the reverse side of the condyles which serve for the reception of bone cement such as is usually employed for the fastening of the femur part 5 to the femur.

The assembly of the exemplary embodiment of the knee joint prosthesis in accordance with the invention shown in FIG. 2 is now done as follows. After the tibia and the femur of the patient have been prepared, the respective desired anchoring shaft 12 is connected to the anchoring section 11. The tibia part 1 is thereby practically complete. The tibia part 1 can now be fastened to the tibia in a known manner.

The anchoring shaft 53 is correspondingly connected to the anchoring section 52, through which the femur part 5 has been completed. The femur part 5 is now fastened in a known manner to the femur.

The "modular" design of the prosthesis, thus the fact that the respective ideal anchoring shaft for the tibia part and the femur part can practically still be chosen in the operating room, ensures the provision of the patient with a prosthesis which is practically "made to measure". But theoretically the tibia part and the femur part can also already be present as an integral part, thus the anchoring shafts can be connected to the respective prosthesis part. This would however either restrict the flexibility of the surgeon in the choice or there would simply have to be a sufficiently large selection of prosthesis parts present at the operation. The "modular" design of the prosthesis considerably reduces the number of parts which must be available in order to have a large selection possibility and finally to ensure the provision of the patient with a prosthesis which is ideal for him.

Now the tibia part 1 has no guide piece for the bearing body 3 (meniscus part) in the previously described assembly. For this purpose the pin 2 is now inserted into the bore 13, which is formed as a blind hole, of the tibia part 1 and is received by this bore 13 in a rotationally fixed manner (as explained above). Theoretically however the guide part could also be formed directly at the tibia part (it could thus be an integral constituent of the tibia part); the manufacture of the tibia part however becomes thereby more complicated and expensive.

Then the bearing body 3—the meniscus part—is inserted in that the upper region 22 of the pin 2 is introduced into the elongate hole 32 of the bearing body 3. Afterwards the circular cylindrical region 40 of the pin 4 is inserted into the circular cylindrical bore 23, which is formed as a blind hole, of the pin 4. These are all procedures which can be carried out by the surgeon during the implantation in an extremely simple manner.

Now the tibia part 1 and the femur part 5 still have to be coupled. This coupling procedure is now considerably simplified in that the pin 4, the coupling member, extends in the direction of the longitudinal axis 14 of the tibia part 1 or, if the bore 13 is not arranged centrally in the tibia part 1, in the direction of an axis parallel to the longitudinal axis 14 of the tibia part. Thereby no complicated threading process results, but rather the femur and the tibia need only be moved in such a manner that the pin 4 is guided into the stabilization box 51 of the femur part, which is a comparatively simple to perform, uncomplicated procedure. The tibia part 1 and the femur part 5 of the prosthesis are thereby coupled and the pure implantation procedure is practically complete.

The design of the condyles 50 of the femur part 5 and of the bearing scallops 31 has already been pointed out. In the extension (e.g. when standing) the prosthesis is usually stressed by large forces (since the weight of the body is placed on the prosthesis when standing). The large forces are admittedly distributed over a large area through the high congruence in the extension, which lowers the surface pressure. As a result of the large forces and the high congruence of the arched surfaces, however, a rotation of the femur part 5 relative to the tibia part 1 is practically not possible in the extension.

If a movement now takes place, then the bearing body 3 moves in the sagittal, posterior direction, which also corresponds to the natural movement when bending the knee. However, the movement of the bearing body 3 in the posterior direction is limited by the elongate hole 32. In the flexion, particularly in a state of strong bending, the congruence is however low, up to the point of a line-shaped contact, because the radius of curvature of the condyles 50 is significantly smaller here than the radius of curvature of the bearing scallops 31 of the bearing body 3. The femur part 5 and the tibia part 1 can be rotated with respect to one another in such a state since the pin 4 is of course rotatably journalled in the pin 2.

If now an extension takes place again, then the bearing body 3 again slides on the tibia bearing surface in the sagittal direction, this time however in the anterior direction. This movement of the bearing body 3 is likewise limited by the elongate hole 32. In the state of extension the contact surface is now relatively large, because in the extension the radius of curvature of the condyles 50 corresponds to the radius of curvature of the bearing scallops 31 and thus a high congruence is present. As already described, a rotation of the femur part 5 relative to the tibia part 1 is practically not possible in this state.

Thus the knee joint prosthesis has a behavior in which no rotation between the femur part 5 and the tibia part 1 is possible in the extension, whereas a certain degree of rotation is possible in the flexion. Consequently, the knee joint prosthesis is suitable in particular as an implant for patients in whom both the cross ligaments and the lateral ligaments are either no longer present or are no longer capable of functioning.

Figure 3:
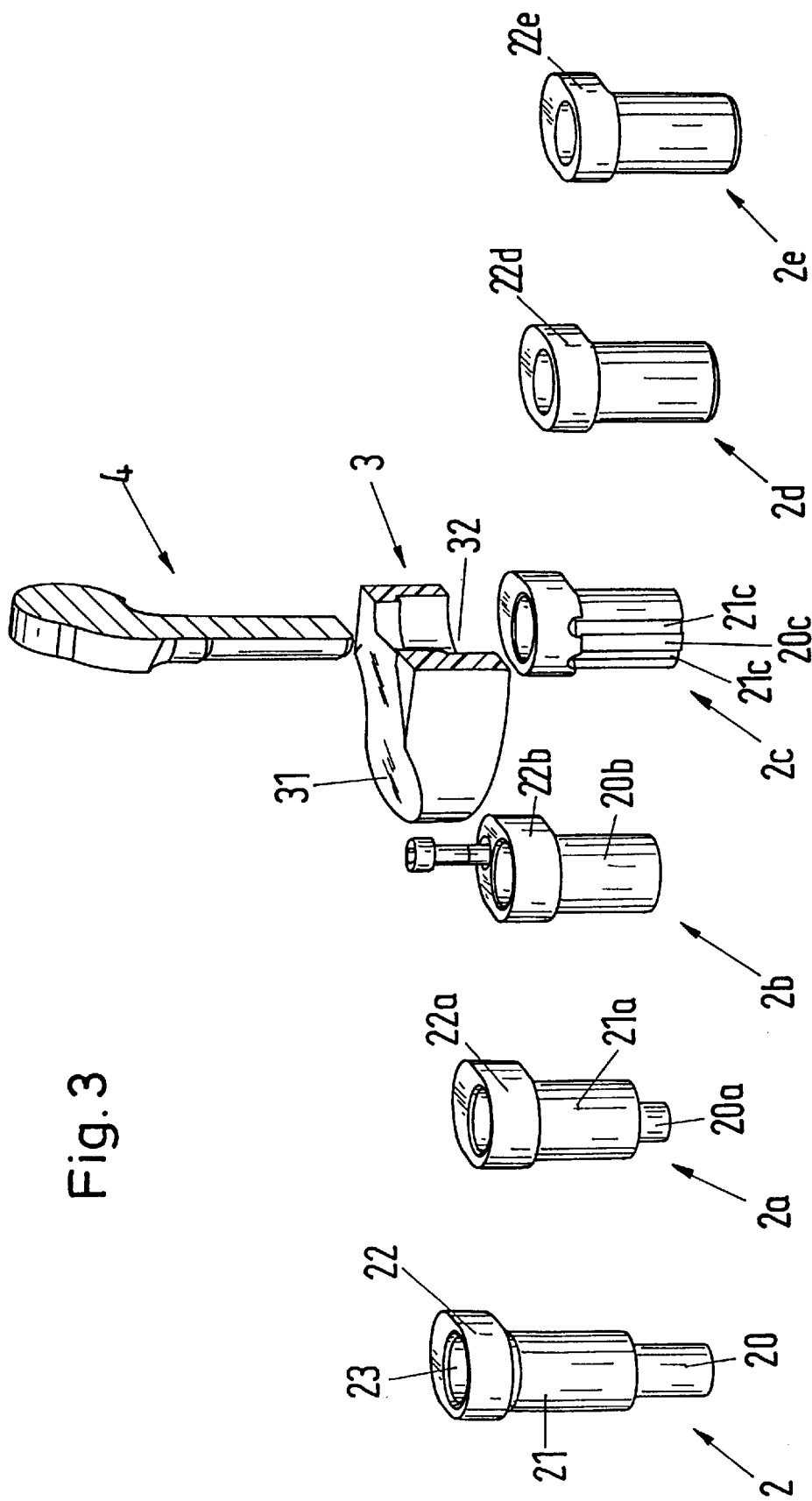
FIG. 3 is an exploded view of an exemplary embodiment of a pin serving as a coupling member, of the bearing body and of various exemplary embodiments of pins which serve as a guide piece.
Figure 4:
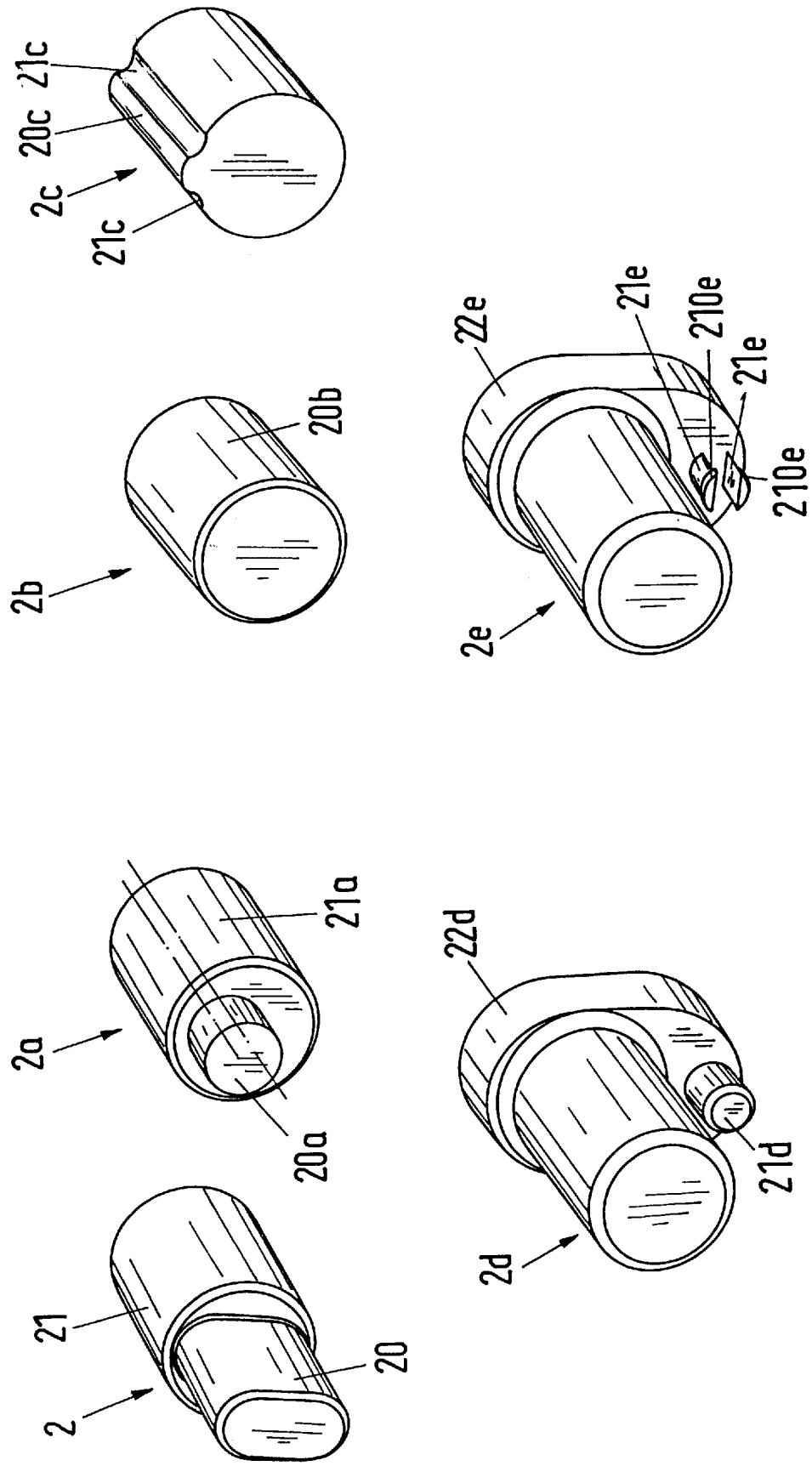
FIG. 4 is a perspective view of the pins of FIG. 2 which form the guide piece, obliquely from below.

In FIG. 3 one recognizes an exploded view of the pin 4 serving as a coupling member, of the bearing body 3, and of various exemplary embodiments of pins 2, 2a, 2b, 2c, 2d, 2e, which serve as a guide piece. FIG. 4 shows these pins which serve as guide pieces or parts of them in a perspective view obliquely from below.

In the exemplary embodiment of the pin 2 shown at the far left in FIG. 3 it is a matter of the exemplary embodiment already explained with reference to FIG. 2. The rotationally fixed arrangement of the pin 2 is based on the oval form of the lower region 20, which engages into a correspondingly formed region of the bore 13 (FIG. 2). One recognizes the oval form of the region 20 even better in FIG. 4, where this exemplary embodiment of the pin 2 is likewise shown at the far left (upper row). The illustration of the upper region 22 of the pin 2 has been dispensed with here.

In the exemplary embodiment shown second from the left in FIG. 3 the rotationally fixed arrangement of the pin 2a is done in such a manner that the middle region 21a and the associated region of the bore in the tibia part 1 are formed as circular cylinders. The lower region 20a is admittedly likewise formed as a circular cylinder, but is axially displaced with respect to the longitudinal axis of the middle region 21a, which can be seen better in FIG. 4 where the middle region 21a and the lower region 20a are shown (second example from the left, upper row). The two regions 20a and 21a can thus be rotated in the respectively associated section of the bore 13 only about different axes, which immediately leads to a blocking when a rotation of the pin is attempted.

Figure 5:
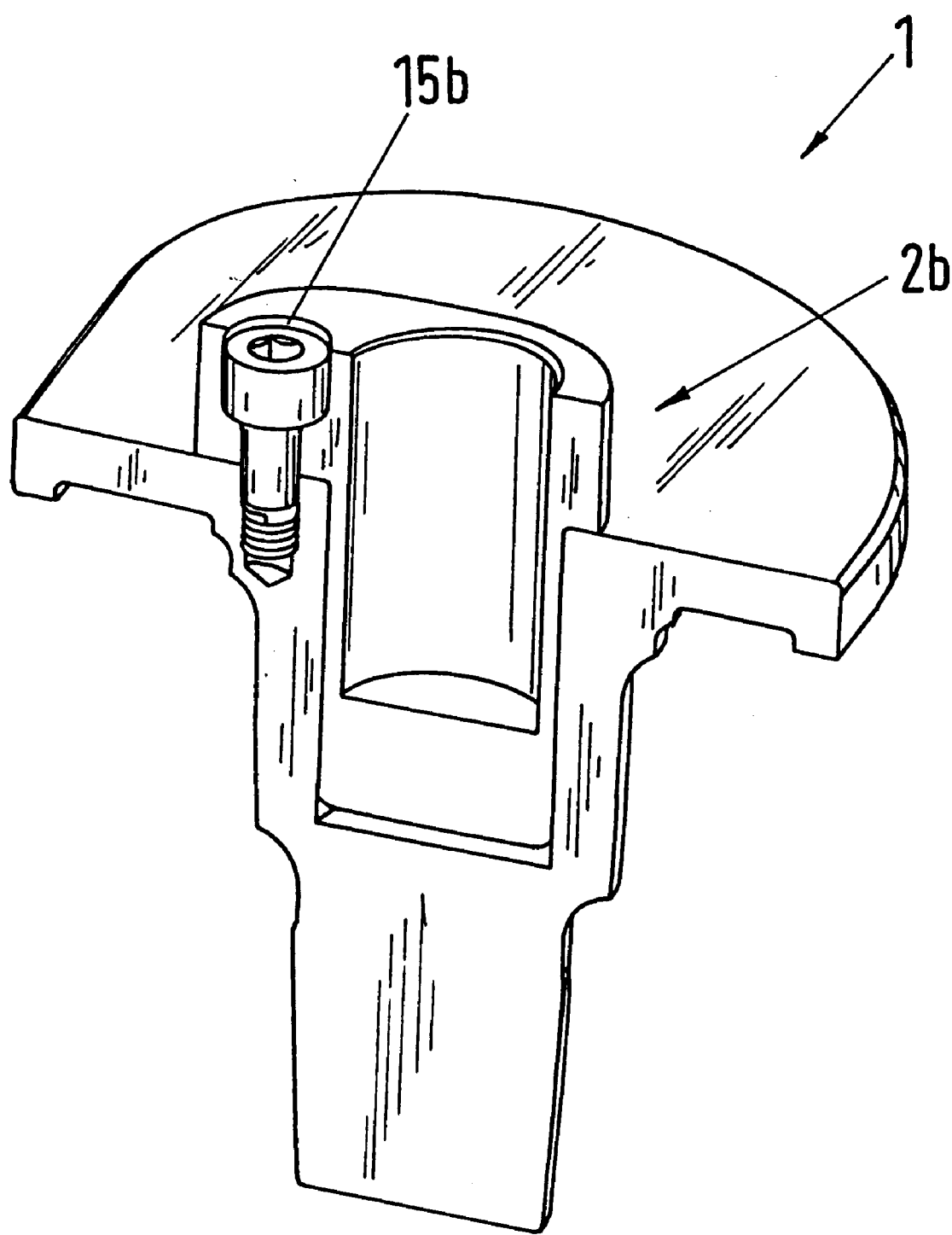
FIG. 5 is an exemplary embodiment of a tibia part in which a pin serving as a guide piece is anchored by means of a screw connection.

In the exemplary embodiment shown third from the left in FIG. 3 the rotationally fixed securing of the pin 2b by means of a separate anchoring of the pin 2b is done with the help of a screw connection. For this, however, the tibia part 1 has an additional bore 15b, which is formed as a threaded blind hole (FIG. 5). The lower region and the middle region of the pin 2b have been brought together to a common, circular cylindrical lower region 20a (see also FIG. 4, second example from the right in the upper row) since of course the fixing is not done via the geometrical form of these regions. This exemplary embodiment is shown once again in FIG. 5 in an illustration of the already assembled and fixed state.

In the exemplary embodiment shown third from the right in FIG. 3 the rotationally fixed arrangement of the pin 2c is done through a projection 20c extending in the longitudinal direction of the pin and through grooves 21c running in the longitudinal direction of the pin on both sides, to the left and to the right of this projection 20c (see also the example at the far right in the upper row of FIG. 4). The lower and the middle regions of the pin 2c have here again also been brought together to a single region. The two exemplary embodiments 2d and 2e which are illustrated at the right in FIG. 3 appear to show no difference at first glance. If one considers the lower row in FIG. 4, however, one recognizes that in the case of the pin 2d, it has a separate pin 21d at its upper region 22d. Alternatively, instead of the separate pin 21d, a bore which is executed as a blind hole can also be provided in the upper region 22d in which a stud which can be separately manufactured can be fixed (e.g. pressed in). In this exemplary embodiment (FIG. 4, lower row, left) a corresponding bore is then provided in the tibia part 1 which receives this pin 21d (or the stud). In this case as well, the pin 2d serving as a guide piece is thereby arranged in a rotationally fixed manner with respect to the tibia part 1.

Figure 6:
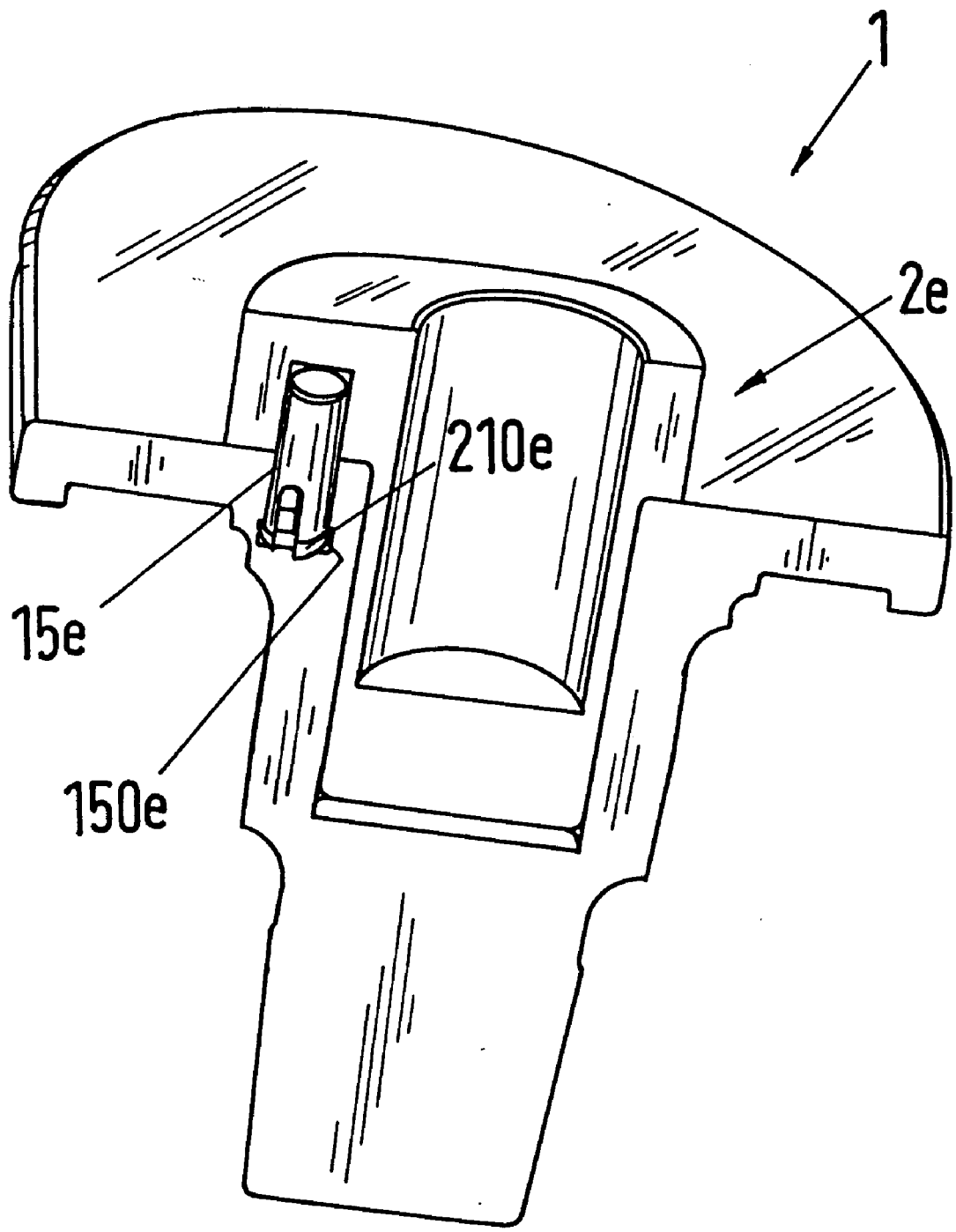
FIG. 6 shows a further exemplary embodiment of a tibia part in which a further exemplary embodiment of a pin serving as a guide piece is anchored.

In the pin 2e (FIG. 4, lower row on the right) two resilient elements 21e with projections 210e are provided instead of the separate pin and are introduced into a corresponding bore 15e in the tibia part 1, which is formed as a blind hole. The separate bore 15e has an undercutting 150e into which the projections 210e of the resilient elements 21e engage. An exemplary embodiment of this kind is shown once again in FIG. 6 in an illustration of the assembled state. The resilient elements 21e in this situation can be formed directly at the pin 2e (and thus form an integral constituent of the pin), as can be recognized in FIG. 4 (to the right in the lower row). A bore which is correspondingly formed as a bind hole can however also be provided in the upper region 22e of the pin 2e into which a stud which can be manufactured separately with correspondingly resilient elements can be fixed, as shown in FIG. 6. One recognizes here that many further variants of the rotationally fixed arrangement which serves as a guide piece are still possible, for which those discussed here are to be considered as exemplary.

Finally, it should also be remarked that the tibia part 1, the pin 2 which is formed as a guide piece, the pin 4 as well as the femur part 5 are typically manufactured of a metal or a metallic alloy such as are usually used in joint prostheses, whereas the bearing body 3 is typically manufactured of a plastic (e.g. polyethylene).

Figure 7:
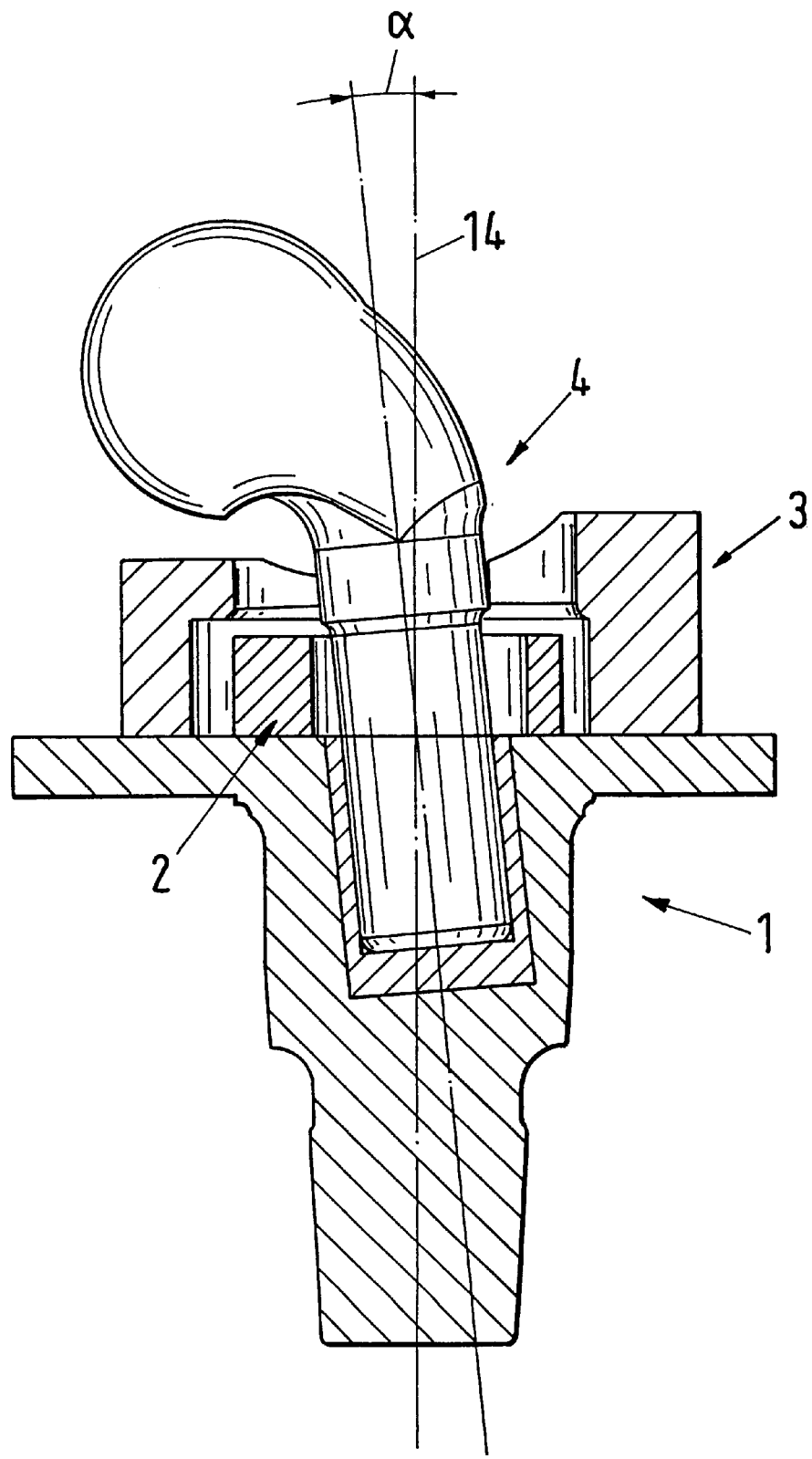
FIG. 7 shows a further exemplary embodiment of a knee joint prosthesis in accordance with the invention (without a femur part).

Finally, FIG. 7 shows a further exemplary embodiment of a knee joint prosthesis in accordance with the invention (in a sectional representation), with the femur part 5 not being illustrated. The essential difference from the above explained variants consists in the fact that the pin 4 is arranged here at an inclination by an angle $\alpha$ with respect to the longitudinal axis 14 (or with respect to an axis parallel thereto). Typically, this angle $\alpha$ amounts only to a few degrees, e.g. up to about 15 degrees. Otherwise the knee joint prosthesis can in principle be constructed in a manner similar to the knee joint prosthesis explained with reference to FIGS. 2 to 6.

In summary, the knee joint prosthesis comprises a tibia part having a tibia bearing surface and a bearing body which is slidingly displaceably journalled on the tibia bearing surface and which has bearing scallops on its side which is remote from the tibia bearing surface. Furthermore, it comprises a femur part which is movably arranged on the bearing scallops of the bearing body as well as a guide piece which is arranged to be rotationally fixed relative to the tibia part and which permits only a displacement of the bearing body in the sagittal direction relative to the tibia bearing surface. Furthermore, it comprises a coupling member which cooperates both with the guide piece and with the femur part and permits a rotation of the femur part on the bearing body. The coupling member has a rotatably journalled pin which extends in the direction of the longitudinal axis of the tibia part or of an axis of rotation parallel to it or in the direction of an axis which is inclined relative to the longitudinal axis of the tibia part or to an axis of rotation parallel to it.

What is claimed is:

1. Knee joint prosthesis comprising a tibia part having a tibia bearing surface, a bearing body which is slidingly and displaceably journalled on the tibia bearing surface and which has bearing scallops on its side remote from the tibia bearing surface, a femur part which is movably arranged on the bearing scallops of the bearing body, a guide piece which is rotationally fixed relative to the tibia part and permits displacement of the bearing body in only a sagittal direction relative to the tibia bearing surface, a coupling member which cooperates with the guide piece and with the femur part and permits rotation of the femur part on the bearing body, the coupling member including a rotatably journalled pin which generally extends in the direction of a longitudinal axis of the tibia part, the guide piece and the coupling member being formed as separate pins, the pin serving as a guide piece and the tibia part forming an arrangement for non-rotationally fixing the pin serving as a guide piece in the tibia part.

2. Knee joint prosthesis in accordance with claim 1, wherein the pin serving as a coupling member has a stabilization piece at its end near the femur parts and wherein femur part has corresponding stabilization surfaces which cooperate with the stabilization piece.

3. Knee joint prosthesis in accordance with claim 1 wherein the pin serving as a coupling member is received in a bore provided in the guide piece in which the pin is rotatably journalled.

4. Knee joint prosthesis in accordance with claim 1 wherein the guide piece is formed on the tibia part.

5. Knee joint prosthesis in accordance with claim 1 wherein the tibia part has an anchoring section which can be connected to a separate anchoring shaft.

6. Knee joint prosthesis in accordance with claim 1 wherein the femur part has an anchoring section which can be connected to a separate anchoring shaft.

7. Knee joint prostheses in accordance with claim 1 wherein the rotatably journalled pin of the coupling member has an axis that is substantially parallel to the longitudinal axis of the tibia part.

8. Knee joint prostheses in accordance with claim 1 wherein the rotatably journalled pin of the coupling member has an axis which is angularly inclined relative to the longitudinal axis of the tibia part.

9. Knee joint prosthesis comprising a tibia part having a tibia bearing surface, a bearing body which is slidingly and displaceably supported on the tibia bearing surface and which has bearing scallops on its side remote from the tibia bearing surface, a femur part which is movably arranged on the bearing scallops of the bearing body, a guide pin which is removably carried by and rotationally fixed relative to the tibia part and permits displacement of the bearing body in only a sagittal direction relative to the tibia bearing surface, and a coupling member which cooperates with the guide pin and with the femur part and permits rotation of the femur part on the bearing body, the coupling member including a rotatable pin which generally extends in the direction of a longitudinal axis of the tibia part.

10. A knee joint prosthesis in accordance with claim 9 wherein the rotatable pin is rotatably journalled in the guide pin.

11. A knee joint prosthesis in accordance with claim 10 wherein the rotatable pin is removably journalled in the guide pin.

12. A knee joint prosthesis in accordance with claim 11 wherein the rotatable pin removably engages the femur part.

* * * * *

UNITED STATES PATENT AND TRADEMARK OFFICE
CERTIFICATE OF CORRECTION

PATENT NO. : 6,099,570  
DATED : August 8, 2000  
INVENTOR(S) : Pascal Livet et al.

Page 1 of 1

It is certified that error appears in the above-identified patent and that said Letters Patent is hereby corrected as shown below:

<u>Title page</u>,
Item [54], please change the title of invention to read -- KNEE JOINT PROSTHESIS --

Signed and Sealed this

Eighth Day of January, 2002

*Attest:*

*Attesting Officer*

JAMES E. ROGAN  
*Director of the United States Patent and Trademark Office*